United States Patent [19]
Smulewicz

[11] 3,967,128
[45] June 29, 1976

[54] INFANT IMMOBILIZING DEVICE

[75] Inventor: Jan J. Smulewicz, New York, N.Y.

[73] Assignee: Nuclear Associates, Inc., Westbury, N.Y.

[22] Filed: Aug. 20, 1974

[21] Appl. No.: 499,100

[52] U.S. Cl. .............................. 250/444; 250/451; 250/456
[51] Int. Cl.² ........................................ G01N 21/34
[58] Field of Search ........... 250/439, 444, 451, 452, 250/456, 521, 519, 515; 269/328

[56] References Cited
UNITED STATES PATENTS

| | | | |
|---|---|---|---|
| 2,794,128 | 5/1957 | Shasky | 250/519 |
| 3,215,834 | 11/1965 | Tayman | 250/451 |
| 3,650,523 | 3/1972 | Darby, Jr. | 269/328 |
| 3,723,743 | 3/1973 | Brackenbrough | 250/515 |
| 3,766,384 | 10/1973 | Anderson | 250/451 X |
| 3,783,863 | 1/1974 | Kliever | 250/456 UX |

*Primary Examiner*—Davis L. Willis
*Attorney, Agent, or Firm*—Blum, Moscovitz, Friedman & Kaplan

[57] ABSTRACT

An infant immobilizing device capable of supporting an infant thereon in various positions for the performance of operations. The device also includes means for holding and positioning an X-ray film cassette so that a full series of X-rays can be taken without the infant being otherwise held.

4 Claims, 13 Drawing Figures

INFANT IMMOBILIZING DEVICE

BACKGROUND OF THE INVENTION

This invention relates generally to an infant immobilizing device. While such devices have been known and have been used for performing operations and taking X-rays on infants, the devices heretofore known have lacked adequate versatility.

Previously, it had been common practice for an assistant such as a nurse or mother to hold an infant while X-rays are taken. However, it is known that excessive and unnecessary exposure to X-rays can cause damage to the reproductive organs and have other adverse affects. As a result, the N.Y. State Government has promulgated regulations which prohibit individuals of reproductive age from holding infants while X-rays are being taken. As a result, an efficient device is necessary to immobilize the infant and to be able to position the infant in the wide variety of positions necessary to take X-rays of various parts of the body. A device addressed to the problem is shown in U.S. Pat. No. 3,215,834 issued Nov. 2, 1965 to D. L. Tayman. However, the Tayman device has proven inadequate in use.

SUMMARY OF THE INVENTION

Generally speaking, this invention relates to an immobilizing device for infants and small children for X-ray examinations, X-ray treatments, cystoscopic examinations, circumcisions and other operative procedures during which an infant or small child must remain immobile for a period of time. For example, with some techniques, X-rays may be taken at intervals of about one-half hour and if there is movement during the time between the taking of the X-rays, the pictures resulting therefrom may become cloudy and/or distorted and the position may differ from film-to-film making comparison and interpretation difficult.

In X-ray therapy, it is undesirable for healthy tissue to be exposed to damaging doses of radiation and while the rays may be precisely located, it requires complete immobilization to limit the exposed area.

With the device of the present invention, an infant or child may be very quickly immobilized by a single operator without additional help and without the need for another person to hold the child during the examination or operative procedure.

The device of the invention permits the infant to be positioned in a wide variety of positions as may be mandated by the procedure to take place. Should the infant also require intravenous feeding, the device provides a means whereby the feeding may be continued.

Accordingly, it is an object of this invention to provide an improved infant immobilizing device.

Another object of the invention is to provide an improved infant immobilizing device capable of supporting an immobilized infant in a wide variety of positions for examinations and operative procedures.

A further object of the invention is to provide an improved infant immobilizing device having a separable infant support panel on which the infant is immobilized with the panel being supportable in a plurality of positions for a number of purposes without requiring a change of position of the infant with respect to the panel.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENT

Figure 1:
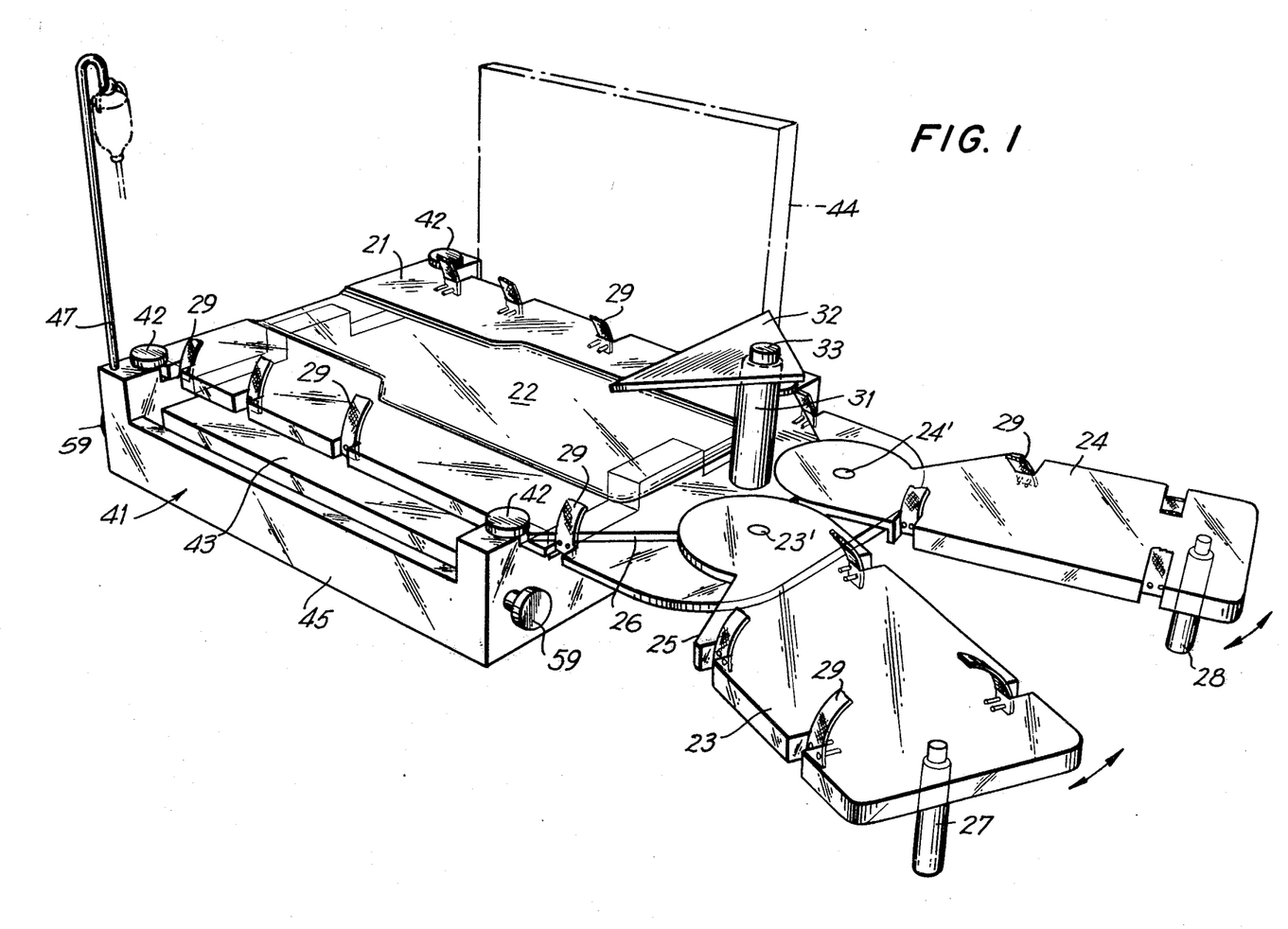
FIG. 1 is a perspective view of an infant immobilizing device constructed in accordance with a preferred embodiment of the instant invention.

An infant immobilizing device constructed in accordance with a preferred embodiment of the instant invention is shown generally in FIG. 1. All components except the X-ray shield are desirably fabricated of materials whose density does not exceed the tissue density of the child so as not to interfere with the transmission of X-rays. Transparent plastic is a highly desirable material although many other materials are equally suitable.

Figures 2, 3:
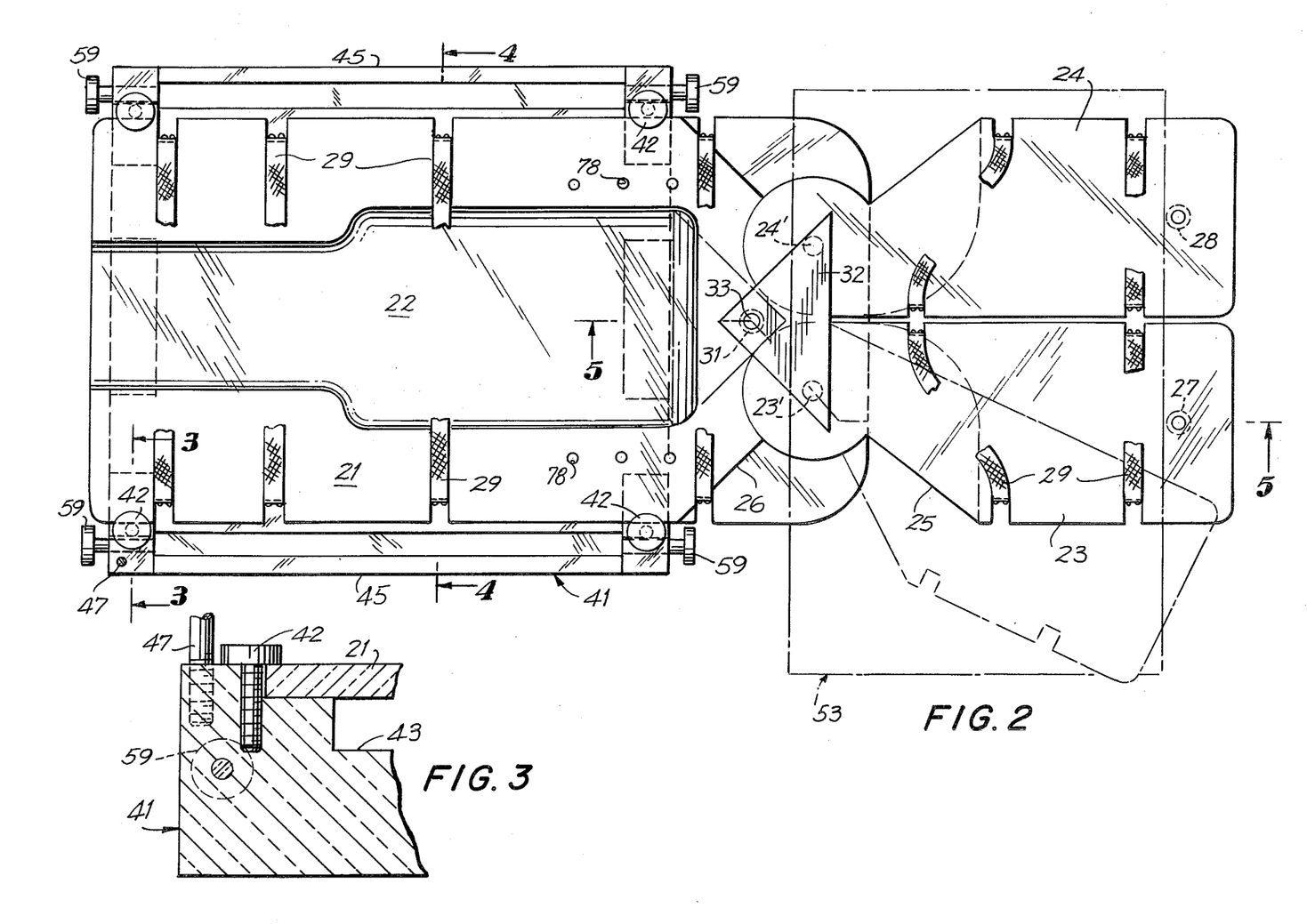
FIG. 2 is a top plan view of the device of FIG. 1 in a modified adjusted position.
FIG. 3 is a partial sectional view taken along line 3—3 of FIG. 2.
Figures 4, 5:
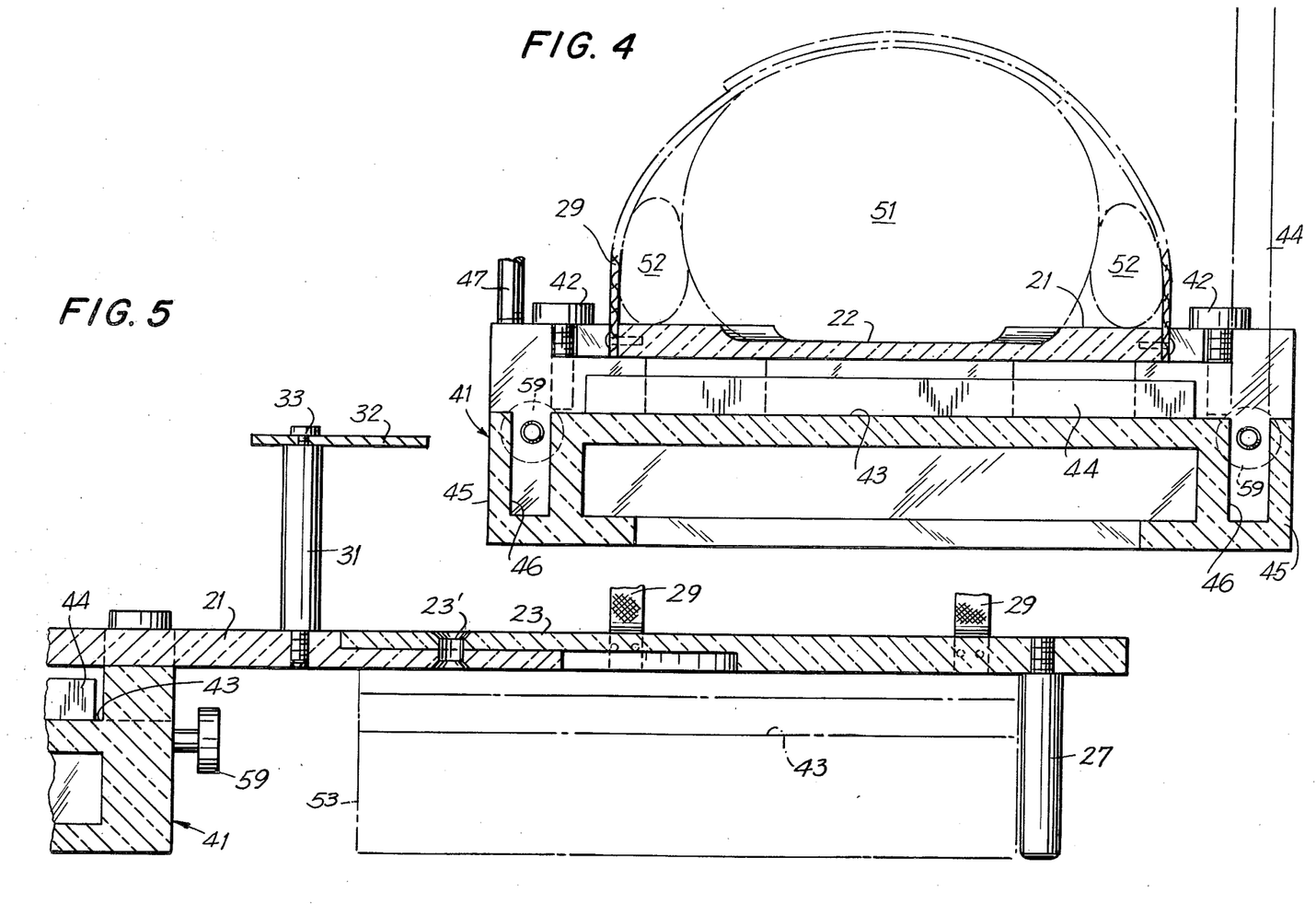
FIG. 4 is a sectional view taken along line 4—4 of FIG. 2.
FIG. 5 is a partial sectional view taken along line 5—5 of FIG. 2.

A generally rectangular body panel 21 is preferably provided with a shallow longitudinal recess 22 to reasonably conform to the shape of the infant who will be strapped thereon. A pair of leg panels 23, 24 are pivoted at one end through pivot pins 23' 24' to one end of body panel 21. Each of leg panels 23, 24 is pivotable about the respective pivot pins in order to position an infant's leg to a selected position. For example, the infant's legs can be spread in order that urological procedures may be conducted. The cross sectional configuration of body panel 21 and leg panel 23 at the pivot point is best seen in FIG. 5 where the top surface of leg panel 23 is shown as a continuation of the top surface of body panel 21. An angular surface 25 on leg panel 23 is adapted for engagement with an angular surface 26 (FIGS. 1 and 2) to limit the outward rotation or degree of pivotal movement of leg panel 23 with respect to body panel 21. Leg panel 24 cooperates with body panel 21 in an identical manner.

Each leg panel 23, 24 carries a removable support leg 27, 28 to support the leg panel portions of the child support plate.

Body panel 21 and leg panels 23, 24 are provided with a plurality of straps 29 removably secured to the panels. The straps are shown in broken away view in FIG. 1 with a typical complete strap 29 being shown in FIG. 4. The straps are preferably fabricated of material known by the trademark VELCRO so as to simplify the securing and removal of the infant to the panels for immobilizing the infant on the panels.

Once the infant has been strapped to the panels, the infant may be transported thereon and placed in a wide variety of positions on the support frames to be hereafter described for a variety of examinations and treatments. As best seen in FIGS. 1 and 5, a post 31 is threadedly engaged in body panel 21 for selective use. The post 31 is adapted to be positioned at the child's crotch to aid in supporting the child when the child is in the vertical position shown in FIG. 8 and to also removably support a lead shield 32 held by a screw 33. The lead shield can be rotated 360° to properly protect the genital areas of male and female infants during X-ray examinations and treatments.

A frame 42 of generally rectangular construction receives body panel 21 when the infant is to be supported in a horizontal position. Body panel 21 is slidable longitudinally in frame 41 for the desired selective positioning of the infant and knobs 42 (FIG. 3) can be tightened to fix the selected position of body panel 21 with respect to frame 41.

Frame 41 includes a shelf 43 spaced below the lower surface of body panel 21 by a distance at least slightly greater than the thickness of the usual X-ray film cassette. A film cassette 44 can be slid into position between shelf 43 and body panel 21 for X-ray examination and by sliding body panel 21 on frame 41, the torso and head of the infant can be properly positioned for taking X-rays from above as desired.

The lateral side walls 45 of frame 41 are spaced from shelf 43 (FIG. 4) by a distance at least slightly greater than the thickness of the usual film cassette. The slot 46 thereby formed can be used to support film cassette 44 shown in phantom in FIG. 4 at either side of the infant to provide for X-ray examination from the side rather than from above. If it is necessary that the infant be fed intravenously or receive a transfusion, a support post 47 may be threaded into frame 41.

An infant's torso 51 and arms 52 are shown in phantom in FIG. 4.

Figure 6:
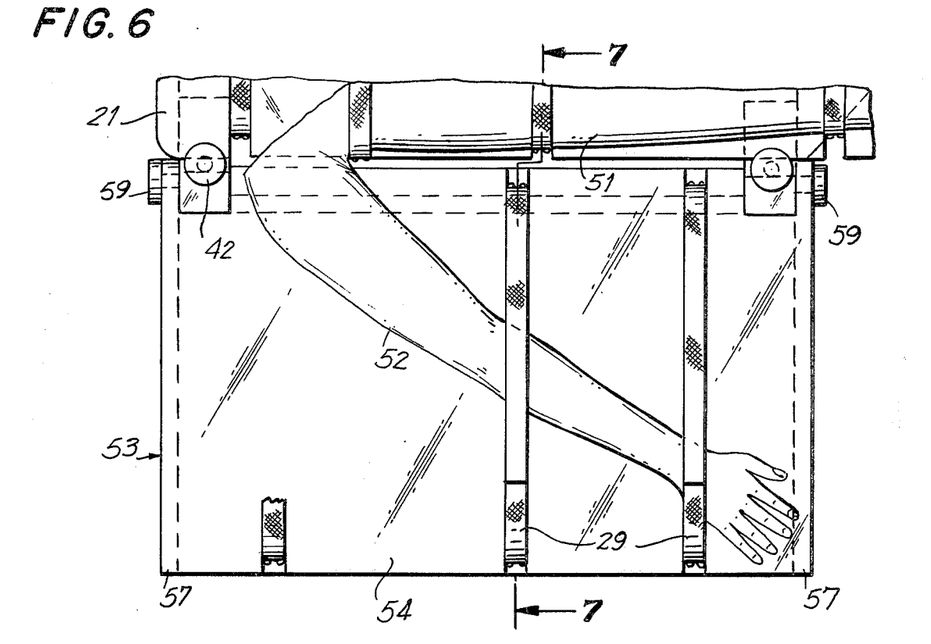
FIG. 6 is a partial top plan view of the infant immobilizing device with an arm supporting attachment.
Figure 7:
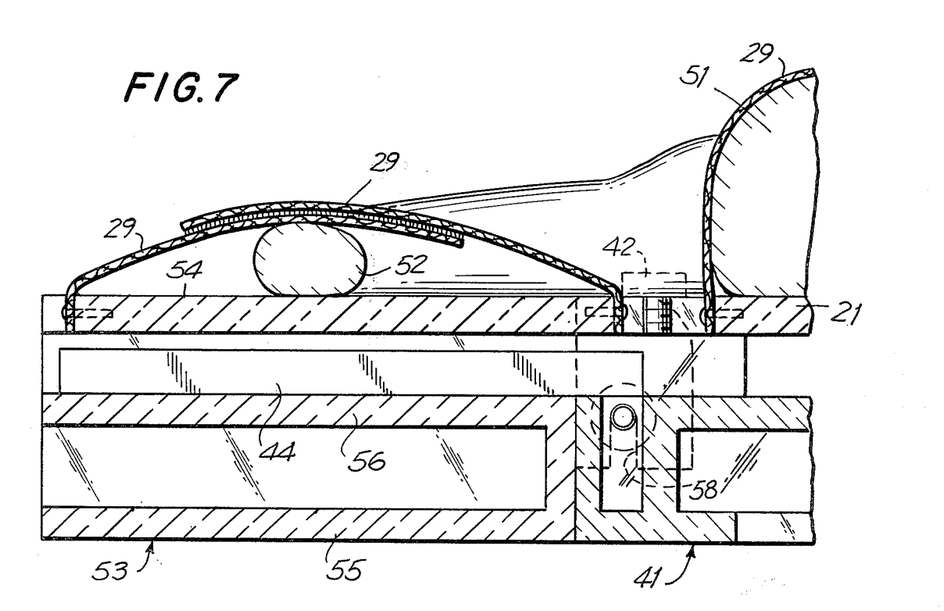
FIG. 7 is a partial sectional view taken along line 7—7 of FIG. 6.

In certain procedures it may be desirable to position the infant with an outstretched arm. In such instances, a secondary frame 53 is provided as shown in FIGS. 6 and 7. The secondary frame has a top panel 54 which carries straps 29 and a base member 55 including a shelf 56. The top surface of shelf 56 is spaced below the bottom surface of top panel 54 a distance at least slightly greater than the thickness of the usual film cassette so that the cassette may be positioned on shelf 56 for X-ray examination of an arm. Secondary frame 53 is also provided with side walls 57 having U-shaped slots 58 which hook on to knobs 59 threaded onto frame 41 to releasably latch secondary frame 53 to frame 41. If both of the infant's arms are to be positioned outwardly and immobilized in such position, it is apparent that two secondary frames 53 would be utilized.

If it is desired that X-ray examinations be conducted of the leg portions of the infant, secondary frame 53 can be positioned beneath leg panels 23 and 24. Secondary frame 53 is shown in phantom in FIGS. 2 and 5.

Figures 8, 9:
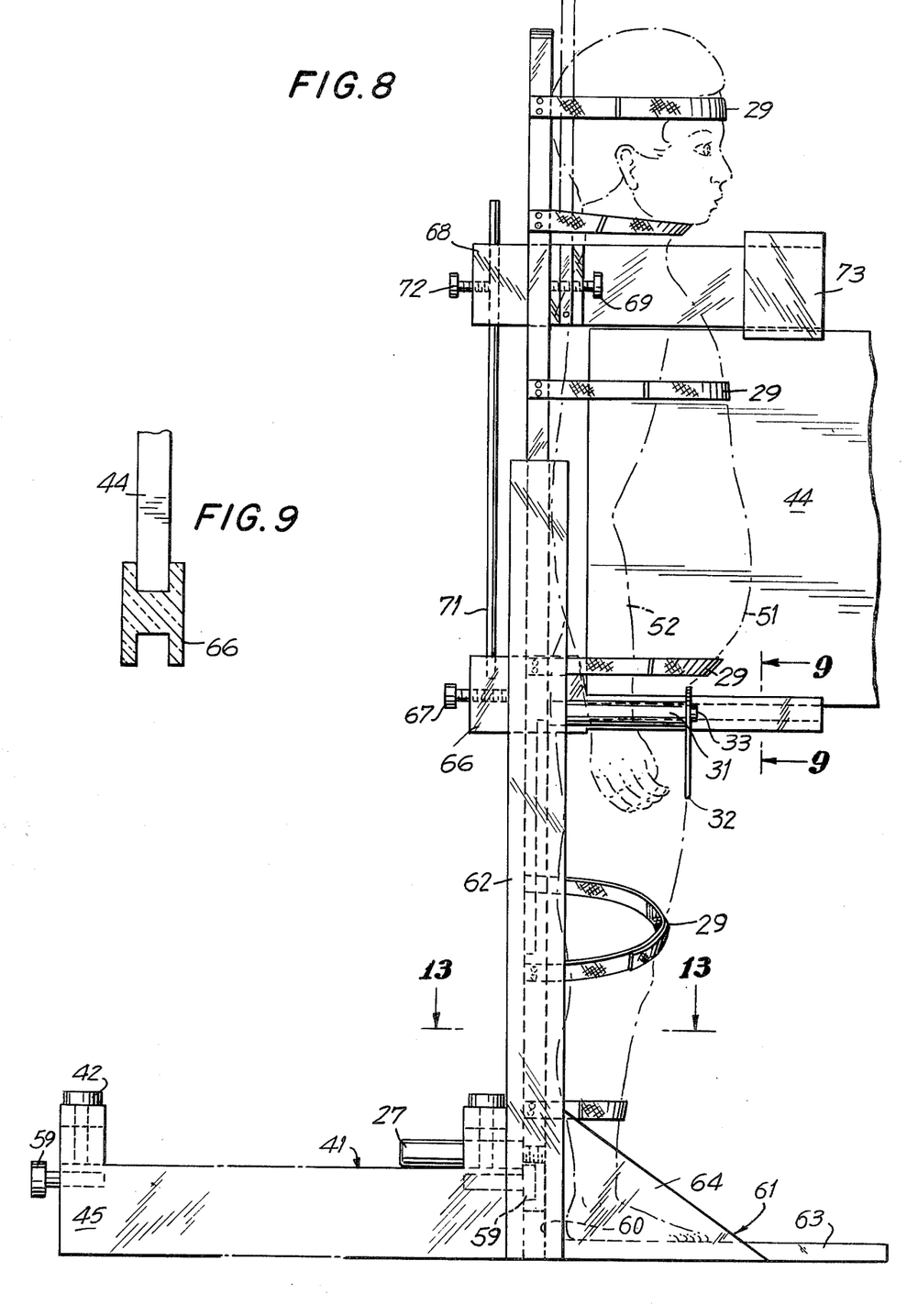
FIG. 8 is an elevational view of the infant immobilizng device with the infant positioned vertically.
FIG. 9 is a partial sectional view taken along line 9—9 of FIG. 8.
Figure 13:
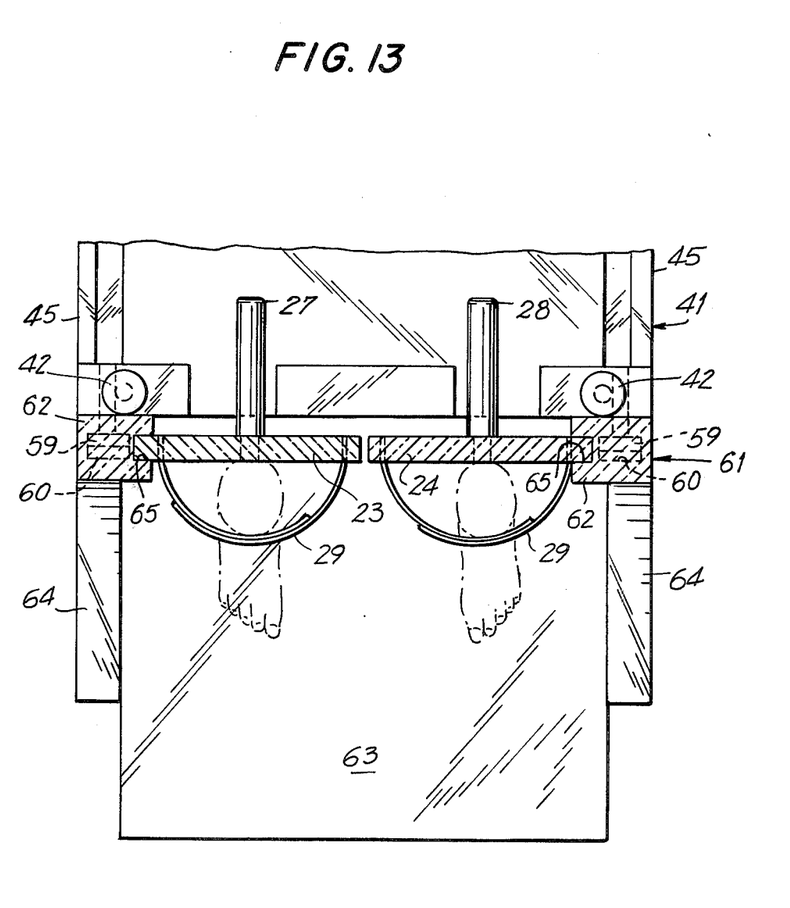
FIG. 13 is a partial sectional view taken along line 13—13 of FIG. 8.

Referring now to FIG. 8, an infant is shown immobilized in an upright position. As best seen in FIGS. 8 and 13, frame 41 has connected thereto a supporting frame 61 which includes a pair of vertical rails 62 joined to a base plate 63 through wedges 64. Supporting frame 61 is releasably secured to frame 41 by use of knobs 59. The heads of knobs 59 are received in mating T-slots 60 (FIG. 13) extending into rails 62 from the bottom ends thereof.

The lateral edges of body panel 21 and leg panels 23 and 24 are received between rails 62 which are provided with longitudinal grooves 65. As viewed in FIG. 8, the infant is prevented from tilting forwardly by means of base plate 63 and wedges 64 and is prevented from tilting rearwardly by the attachment of supporting frames 61 to frame 41 and by the mutual cooperation between removable support legs 27, 28 and frame 41.

Figure 10:
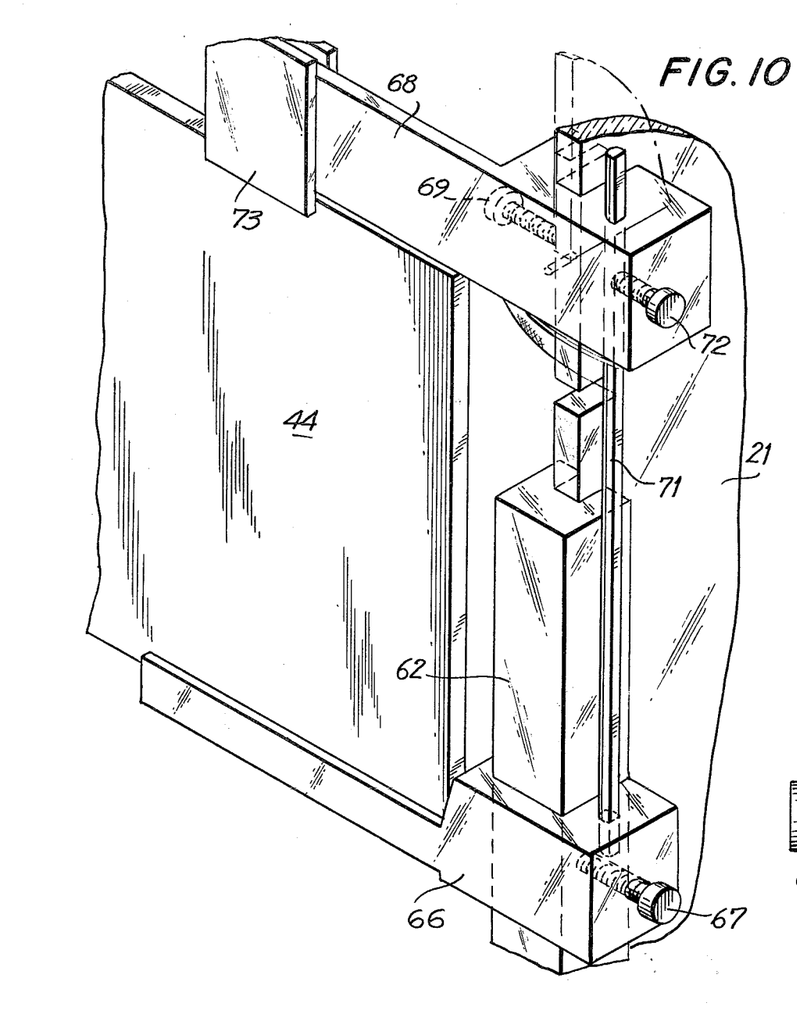
FIG. 10 is a perspective view of a film cassette supporting arrangement for a sideview X-ray when the infant is in a vertical position.
Figures 11, 12:
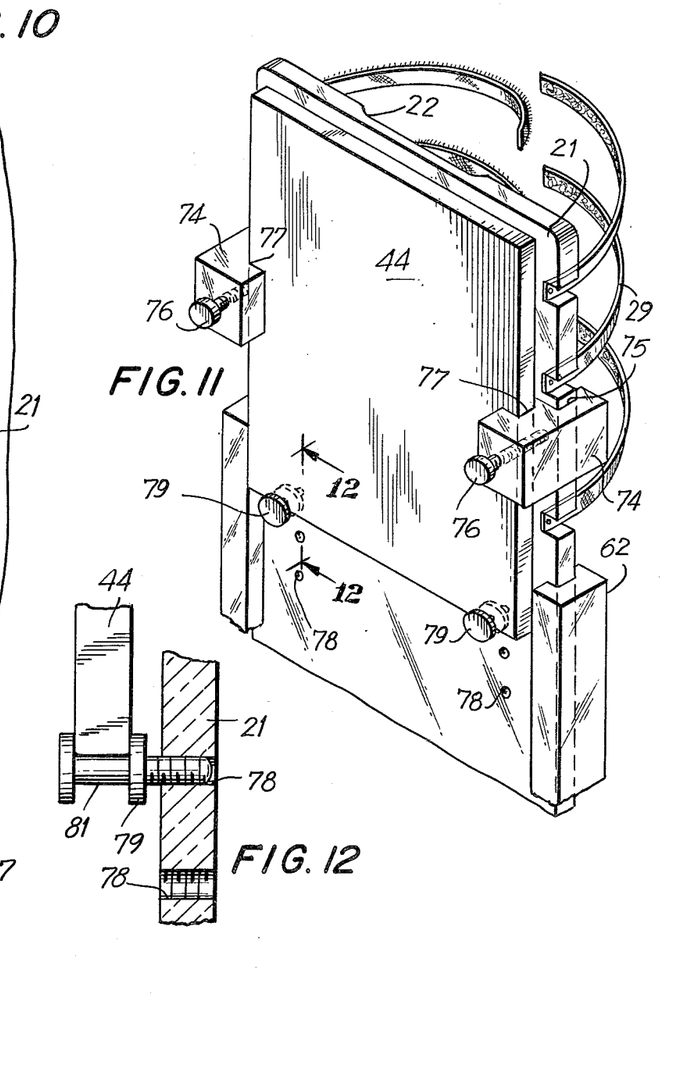
FIG. 11 is a perspective view of a film cassette supporting arrangement for a front view X-ray when the infant is in a vertical position.
FIG. 12 is a partial sectional view taken along line 12—12 of FIG. 11.

Means are also provided for positioning X-ray film cassettes for taking X-rays in frontal and lateral directions. As best seen in FIGS. 8, 9 and 10, the lower arm 66 is removably mounted to a rail 62 by means of a threaded pin 67. Lower arm 66 has a cross sectional configuration shown in FIG. 9 to receive a film cassette 44. An upper arm 68 is removably secured to body panel 21 by means of a threaded pin 69. A rod 71 is secured in lower arm 66 and passes slidably through upper arm 68 so that the distance between the lower and upper arms may be preset as determined by the height of the film cassette. A threaded pin 72 locks rod 71 in upper arm 68. Upper arm 68 carries a bracket 73 to overfit with the top edge of film cassette 44. The means just described is used to take a side view X-ray with the infant in the vertical position. The means for taking a view through the front with the infant in the vertical position is shown in FIGS. 11 and 12.

A pair of bracket members 74 each have a first groove 75 in which is received an edge of body panel 21. A threaded pin 76 secures the bracket member to the body panel in any selected position. Each of the bracket members 74 is also provided with a second groove 77 to slidably receive the edge of the film cassette and position it rearwardly of body panel 21. Body panel 21 is also provided with a plurality of threaded holes 78 adapted to receive support pins 79. The support pins are provided with annular grooves 81 to receive and support the bottom edge of film cassette 44. Thus, by adjusting the location of bracket members 74 and support pins 79, the film cassette can be positioned as desired in the vertical plane.

From the foregoing description, it can be seen that the basic components of the panel assembly on which the infant is immobilized and the basic frame (frame 41) allow examinations, treatments and operations to be performed on an immobilized child without the need of an assistant. By adding certain other elements to the basic components, an infant can be immobilized in horizontal and vertical positions for a wide variety of treatments and examinations including the complete range of X-ray examinations.

It will thus be seen that the objects set forth above, and those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An infant immobilizing device comprising a frame for support by a horizontal surface, a body panel, restraining means for releasably restraining an infant on said body panel, means cooperating between said body panel and said frame for removably and adjustably securing said body panel to said frame with the infant oriented substantially horizontally and with the infant oriented substantially vertically, and cassette support means carried by said body panel for vertically supporting an X-ray film cassette in relation to the infant when the infant is oriented substantially vertically.

2. An infant immobilizing device as claimed in claim 1, and including a post removably secured to said body panel and an X-ray shielding member removably secured to said post, said X-ray shielding member having a major X-ray shielding portion, said X-ray shielding member being pivoted on said post for positioning of the major X-ray shielding portion between at least two positions disposed substantially 180° apart.

3. An infant immobilizing device as claimed in claim 1, wherein said frame and said body panel define an assembly, and further including second and third cassette support means cooperating with said assembly for supporting an X-ray film cassette, said second support means for positioning said cassette horizontally when the infant is oriented substantially horizontally and said third support means for positioning said cassette vertically when the infant is oriented substantially horizontally.

4. An infant immobilizing device as claimed in claim 1, wherein said body panel includes a planar portion and a pair of leg portions and pivot means for pivoting each said leg portion to said planar portion.

* * * * *